United States Patent
Romari et al.

(10) Patent No.: US 9,506,100 B2
(45) Date of Patent: *Nov. 29, 2016

(54) **PRODUCTION OF ASTAXANTHIN AND DOCOSAHEXAENOIC ACID IN MIXOTROPHIC MODE USING *SCHIZOCHYTRIUM***

(71) Applicant: FERMENTALG, Libourne (FR)

(72) Inventors: Khadidja Romari, Clermont-Ferrand (FR); Adeline Le Monnier, Surzur (FR); Cyril Rols, Libourne (FR); Cindy Merlet, Saint Denis de Pile (FR); Julien Pagliardini, Cenon (FR); Pierre Calleja, Bordeaux (FR); Claude Gudin, Aix en Provence (FR)

(73) Assignee: FERMENTALG, Libourne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/385,294

(22) PCT Filed: Mar. 15, 2013

(86) PCT No.: PCT/FR2013/050547
§ 371 (c)(1),
(2) Date: Sep. 15, 2014

(87) PCT Pub. No.: WO2013/136028
PCT Pub. Date: Sep. 19, 2013

(65) Prior Publication Data
US 2015/0037838 A1    Feb. 5, 2015

(30) Foreign Application Priority Data
Mar. 16, 2012 (FR) ...................... 12 52380

(51) Int. Cl.
*C12P 7/64* (2006.01)
*C12P 23/00* (2006.01)
*C12R 1/89* (2006.01)
*C12N 1/12* (2006.01)

(52) U.S. Cl.
CPC ............... *C12P 23/00* (2013.01); *C12N 1/12* (2013.01); *C12P 7/6427* (2013.01); *C12P 7/6472* (2013.01); *C12R 1/89* (2013.01)

(58) Field of Classification Search
CPC ...... A23L 1/19; C12P 7/6472; C12P 7/6427; C12P 23/00; C12N 1/89; C12N 1/12
See application file for complete search history.

(56) References Cited

U.S. PATENT DOCUMENTS

| | | | | |
|---|---|---|---|---|
| 3,316,674 A | * | 5/1967 | Shirota ................ | A01G 33/00 435/257.3 |
| 3,444,647 A | * | 5/1969 | Masahito ............... | A01G 33/00 210/602 |
| 5,381,075 A | * | 1/1995 | Jordan .................. | C12M 21/02 307/115 |
| 2006/0166343 A1 | * | 7/2006 | Hankamer ............. | C12N 1/12 435/168 |
| 2009/0069213 A1 | * | 3/2009 | Avila ..................... | A61K 8/975 514/1.1 |
| 2009/0117194 A1 | * | 5/2009 | Burja ..................... | A21D 8/04 424/490 |
| 2009/0305942 A1 | * | 12/2009 | Day ....................... | C12P 7/6418 510/437 |

FOREIGN PATENT DOCUMENTS

WO    96/21723    7/1996
WO    2009/134114    11/2009

OTHER PUBLICATIONS

U.S. Appl. Nos. 13/822,805; 13/878,468; 14/124,367; 14/127,389; 14/124,829; 14/385,305; 14/385,502; 14/385,507.*
International Search Report dated Jul. 2, 2013, corresponding to PCT/FR2013/050547.
W. Chatdumrong, et al.; "Optimization of docosahexaenoic acid (DHA) production and improvement of astaxanthin content in a mutant Schizochytrium limacinum isolated from mangrove forest in Thailand"; vol. 41; 2007; pp. 324-334.
Aki Tsunehiro, et al.; "Thraustochytrid as a Potential Source of Carotenoids"; vol. 80, No. 8; Aug. 1, 2003; pp. 789-794.

* cited by examiner

*Primary Examiner* — Ruth Davis
(74) *Attorney, Agent, or Firm* — Young & Thompson

(57) ABSTRACT

New strains of protists belonging to the *Schizochytrium* genus, allow high-yield production of lipids and carotenoids, in particular of astaxanthin and docosahexaenoic acid (DHA), in mixotrophic mode, and a method for selecting and culturing such strains, using a variable and/or discontinuous light source, in particular a flashing light.

18 Claims, No Drawings

PRODUCTION OF ASTAXANTHIN AND DOCOSAHEXAENOIC ACID IN MIXOTROPHIC MODE USING *SCHIZOCHYTRIUM*

The invention relates to a method of culture in mixotrophic mode, in particular in the presence of discontinuous and/or variable illumination with light, of a protist of the Labyrinthulomycetes class, in particular of the genus *Schizochytrium*. The method gives a high yield of biomass and enrichment of the thus cultured microalgae in lipids and carotenoids and more particularly in docosahexaenoic acid (DHA) and astaxanthin. The method thus makes it possible to select strains of *Schizochytrium*, with mixotrophic character, and having a high yield of lipids and/or carotenoids, and more particularly of polyunsaturated fatty acids and astaxanthin. The invention also relates to a novel strain of protist belonging to the genus *Schizochytrium*, particularly adapted to the production of lipids and carotenoids. This novel strain of *Schizochytrium* is useful for producing docosahexaenoic acid (DHA) and astaxanthin in mixotrophic mode.

Preamble

The protists are microorganisms with a simple cellular organization, i.e. they are generally unicellular and sometimes multicellular but without specialized tissues. They may be autotrophic or heterotrophic.

The protists are currently the subject of numerous industrial projects since some species are capable of accumulating or secreting major quantities of lipids, in particular polyunsaturated fatty acids.

*Schizochytrium* is a protist of the Thraustochytriaceae family, a very widespread group of marine fungus. The Thraustochytrids are known to produce a wide range of lipids, in particular polyunsaturated fatty acids, and some species are known to produce carotenoids.

Among the polyunsaturated fatty acids, certain highly unsaturated fatty acids (HUFA) of the omega-3 series (PUFA-ω3), in particular eicosapentaenoic acid (EPA or C20:5 ω3) and docosahexaenoic acid (DHA or C22:6 ω3), and of the omega-6 series (PUFA-ω6), in particular arachidonic acid (ARA or AA or eicosatetraenoic acid C20:4 ω6) have a recognized nutritional importance, and have strong potential in terms of therapeutic applications.

Regarded as an essential nutrient, DHA is necessary to the normal functional development of cells, and plays a crucial role in various biochemical processes and functions. Its polyunsaturated nature confers on it a crucial importance in relation to the properties of the cell membrane, both in plants and in animals: fluidity, flexibility and selective permeability allowing for example effective adaptation, and even survival, at low temperatures, in particular in fish.

DHA is a major structural constituent of the human brain and it is its principal fatty acid. DHA represents 15-20% of the cerebral cortex (an adult's brain contains at least 20 g of DHA) and 30-60% of the retina. It is essential for the development of the central nervous system and for retinal function, by incorporation into the cell membranes, and plays a major role in the acquisition and satisfactory maintenance of the mechanisms of vision and memory.

Fish oils, from the fishing industry, are currently the main commercial source of these types of fatty acids. However, while these oils find new applications (food supplement in aquaculture, incorporation in margarines), marine halieutic resources are becoming scarce because of intensive fishing activity.

Therefore, new sources of these fatty acids such as EPA, DHA and ARA have to be sought in order to meet, in the future, the increasing demand for these types of polyunsaturated fatty acids.

In addition to their capability of synthesizing fatty acids de novo, protists provide several advantages compared to fish oils: they may be cultured in vitro under controlled conditions, which allows production of a biomass of a relatively constant biochemical composition, and, in addition, unlike fish oils, they do not have an unpleasant odour and their lipids contain little or no cholesterol.

Finally, the lipids produced by protists have a simpler fatty acid profile than that of fish oils, which limits the steps for separating the fatty acids of interest.

Furthermore, carotenoids are also molecules of interest. They are generally used as pigments, but they also have an important role for human health as antioxidant agents. Finally, they have the ability to stimulate the immune system.

For implementing the production of fatty acids and carotenoids by protists on an industrial scale, several factors must be taken into account. For example, cultures may be carried out under autotrophic, mixotrophic or heterotrophic conditions depending on the strain, the temperature, the lighting conditions and the size of the fermenters. For example, cultures may also be carried out in 1 L containers, in a laboratory, in photo-bioreactors, and in 100,000 L containers or in open ponds (several hectares). However, the costs of energy and other resources such as manpower and the ease of monitoring the culture must be taken into account for developing ideal culture conditions.

In any case, it is desirable that the protists are cultured under optimum conditions for increasing the yield of the fatty acid(s) and of the carotenoid(s) to be produced. Thus, it is preferable to have a yield that is as high as possible (for example biomass above 80 g/l of dry matter, more than 25% of fatty acids by weight relative to the total weight of dry matter, and for example more than 0.2% by weight of carotenoids to the total weight of dry matter).

The effect of light on growth is not restricted to photosynthetic organisms (plants; cyanobacteria, microalgae and macroalgae). Certain non-chlorophyl organisms have photoreceptors that enable them to capture the light signals that are essential for their development. Photoreceptors such as phytochrome represent a typical example of a light sensor that controls the development of the organism that possesses it. To date, different photoreceptors have been described, namely, among others, the accessory pigments, the cryptochromes and phototropins.

*Schizochytrium* is known to produce DHA in heterotrophic mode as well as astaxanthin, when it is cultured under heterotrophic conditions, in the presence of continuous fluorescent light [R. Poontawe, et al. (2008); Optimization of DHA and astaxanthin production by *Schizochytrium* sp. isolated from mangrove forests in Thailand. JSPS-NRCT core university program on development of thermotolerant microbial resources and their applications, pp. 134-135].

However, from the standpoint of industrial exploitation, this method of culture proves to be unsuitable. In fact, to be profitable, it must be possible for biomass production to be carried out in large, closed photo-bioreactors. Now, such a method of culture is difficult to implement, because when the density of the cells increases in the culture medium, it becomes more and more difficult for the cells to capture the light originating from outside the reactor. It is therefore necessary to actively stir the culture medium, which requires substantial energy expenditure.

It would be desirable to be able to obtain higher yields of DHA and astaxanthin than described in the prior art, for a more efficient and cost-effective industrial production.

To improve the yield of DHA and astaxanthin, an alternative to the method of culture described above would be to conduct culture in mixotrophic mode, i.e. with a supply of light of lower intensity and in the presence of a supply of organic substrate.

It is to be understood that the term mixotrophic is usually employed with regard to strains having a chloroplast, able to develop in the presence of light, using two sources of carbon (organic and inorganic). In the case of the strains of the genus *Schizochytrium*, such a chloroplast has not been identified. However, as the strain is both heterotrophic and reactive to light, the term mixotrophic will be extended in the sense of the invention to this category of strain.

Thus, it was after numerous experiments under unusual lighting conditions and with the addition of various substrates that the applicant succeeded in isolating protist strains of the species *Schizochytrium* that can be cultured in mixotrophic mode, allowing, under the conditions of the present invention, a high-yield production of polyunsaturated fatty acids and carotenoids, notably DHA and astaxanthin.

One strain (FCC 1104) representing novel strains of *Schizochytrium* thus isolated and selected, was deposited at the CCAP (Culture Collection of Algae and Protozoa, Scottish Association for Marine Science, Dunstaffnage Marine Laboratory, Oban, Argyll PA37 1QA, Scotland, United Kingdom) according to the provisions of the Treaty of Budapest, under the accession number CCAP 4087/1.

The method of culture and selection consisted more particularly of culturing the protists under mixotrophic conditions, in the presence of variable and/or discontinuous illumination, notably in the form of flashes, with a range of specific variations of light intensity and frequency.

The frequent alternation of illuminated phases and phases of darkness or of lower light intensity, generally perceived as stressful for protists, surprisingly, made it possible to obtain a high production of biomass, of lipids and more particularly of polyunsaturated fatty acids and carotenoids, from the strains of *Schizochytrium*. The application of such strains according to the invention opens the perspective of industrial production of polyunsaturated fatty acids, in particular of DHA, and of carotenoids, in particular astaxanthin, in fermenters benefiting from a reduced light supply, and should therefore make possible energy savings compared to the methods of culture described above.

The different aspects and advantages of the invention are detailed below.

DETAILED DESCRIPTION

The present invention therefore relates to a method of culture of protists of the Labyrinthulomycetes class, in particular of the Thraustochytrid family, in particular of the genus *Schizochytrium*, in mixotrophic mode, under conditions of illumination that is discontinuous and/or variable over time. The illumination has variations in intensity, the amplitude of which is generally comprised between 5 $\mu mol \cdot m^{-2} \cdot s^{-1}$ and 1000 $\mu mol \cdot m^{-2} \cdot s^{-1}$, preferably between 30 and 400 $\mu mol \cdot m^{-2} \cdot s^{-1}$. These variations may generally take place between 2 and 3600 times per hour, preferably between 2 and 200 times per hour. These culture conditions make it possible to supply a defined quantity of light. This light supply may comprise phases of discontinuous and/or variable illumination, with variations in intensity that may have identical or different amplitudes. The illumination may in particular be in the form of flashes.

The advantage of this method is to increase the yield of biomass obtained from the culture. The other advantage is to enrich the thus cultured protists in polyunsaturated fatty acids, more particularly docosahexaenoic acid (DHA), and in carotenoids, more particularly astaxanthin. This method may also be used for selecting strains of the Labyrinthulomycetes class, notably of the Thraustochytrid and Labyrinthulid families, in particular of the genus *Schizochytrium*, with mixotrophic character, and having a high yield of polyunsaturated fatty acids, in particular DHA, and of carotenoids, in particular astaxanthin.

Culture of this protist in mixotrophic mode is preferably carried out in the presence of 100 mM to 1.5 M, preferably from 300 mM to 1.2 M, more preferentially from 500 mM to 1 M, and even more preferentially from 600 mM to 900 mM of an organic carbon-containing substrate. The substrate is supplied continually during the culture, so as to allow the cells to accumulate a high concentration of lipids and carotenoids. Additional substrate is added to the culture medium during the culture process so as to maintain a constant concentration. This organic carbon-containing substrate comprises preferentially, in pure form or as a mixture: glucose, cellulose derivatives, saccharose and/or glycerol.

The organic carbon-containing substrate contained in the culture medium may consist in complex molecules or in a mixture of substrates. The products resulting from the biotransformation of starch, for example starting from maize, wheat or potato, notably starch hydrolysates, which are constituted of small sized molecules, for example, organic carbon-containing substrates suitable for mixotrophic culture of the protists according to the invention.

This method is more particularly intended for the use of novel strains of the Labyrinthulomycetes class, in particular of the genus *Schizochytrium* (Division: Myxomycota, Order: Saprolegniales, Family: Thraustochytriaceae) [ITIS Catalogue of Life, 2010] selected for their mixotrophic character, and having a high yield of polyunsaturated fatty acids, notably DHA, and of carotenoids, notably astaxanthin, and in particular for their capability to be cultured with a light supply greater than 10 µE, in a medium rich in organic elements, for example modified Verduyn medium (sea salts 15 g/L, $(NH_4)_2SO_4$ 3 g/L, $KH_2PO_4$ 1 g/L, $MgSO_4 \cdot 7H_2O$ 0.5 g/L, $Na_2EDTA$ 24 mg/L, $ZnSO_4 \cdot 7H_2O$ 3 mg/L, $MnCl_2 \cdot 2H_2O$ 3 mg/L, $Na_2MoO_4 \cdot 2H_2O$ 0.04 mg/L, $FeSO_4 \cdot 7H_2O$ 10 mg/L, pantothenate 3.2 mg/L, thiamine hydrochloride 9.5 mg/L, vitamin B12 0.15 mg/L, antifoaming agent 0.1 mL/L), to which an organic carbon-containing substrate is added. Preferably, the organic carbon-containing substrate comprises glucose, glycerol, at a concentration equivalent to or greater than 300 mM.

By "strain", it is meant not only the natural strains of the genus *Schizochytrium*, but also the mutants of said natural strains.

These novel strains of *Schizochytrium* may be isolated and selected by the method of selection and culture according to the invention described hereafter.

A representative strain of the *Schizochytrium* strains according to the invention is the strain FCC 1104 isolated by the applicant and deposited at the CCAP under the accession number CCAP 4087/1. These strains are capable of producing significant quantities of biomass as well as lipids and carotenoids, and more particularly of DHA and astaxanthin when they are cultured in mixotrophic mode with a variable or discontinuous light supply, according to the invention.

According to the ongoing taxonomic analyses, the strain CCAP 4087/1 belongs to the genus *Schizochytrium*. The invention relates to any strain of the Labyrinthulomycetes class, in particular of the genus *Schizochytrium*, capable of growing under mixotrophic culture conditions such as described in the present application, and capable of producing fatty acids, such as DHA, and/or carotenoids, such as astaxanthin. The invention also relates to any species of protist of the genus *Schizochytrium*, capable of growing under mixotrophic culture conditions such as described in the present application, and capable of producing fatty acids, such as DHA, and carotenoids, such as astaxanthin.

The isolated strains of *Schizochytrium* according to the invention make it possible to produce, under mixotrophic conditions, significant quantities of biomass, as well as lipids and carotenoids, the lipids being rich in DHA. Said DHA may represent more than 40%, or more than 50%, or more than 60% of the total lipids contained in the protists, the carotenoids being rich in astaxanthin, and said astaxanthin may represent more than 0.1%, or more than 0.15%, or more than 0.2% by weight of the total weight of dry matter. The strains may reach a level of productivity (quantity of product of interest produced, per liter of culture, per hour) of 0.015 mg/L/h, or more than 0.020 mg/L/h, or more than 0.025 mg/L/h.

In the present invention, the strains of *Schizochytrium* (for example, the strain FCC 1104, isolated by the applicant) that are cultured under mixotrophic conditions in the presence of variable and/or discontinuous illumination, in particular in the form of flashes, allow production of astaxanthin. In contrast, under heterotrophic conditions, no astaxanthin is detectable. Moreover, the quantities of biomass obtained in mixotrophic mode according to certain embodiments of the invention are equal to or even greater than (for example, by approximately 10-18%) the quantities obtained under heterotrophic conditions. By "heterotrophic conditions", it is meant culture conditions with an identical culture medium, but in the absence of light.

The invention thus relates to a method of culture of protest strains of the Labyrinthulomycetes class, notably of the Thraustochytrid families, in particular of the genus *Schizochytrium*, notably of the species *Schizochytrium* sp. as deposited, in mixotrophic mode, in the presence of an illumination that is variable or discontinuous over time, for example in the form of flashes, notably with a view to producing polyunsaturated fatty acids and carotenoids, such as DHA and astaxanthin.

The invention thus relates to a method for selecting protist strains of the Labyrinthulomycetes class, notably of the Thraustochytrid and Labyrinthulid families, in particular, of the genus *Schizochytrium*, notably of the species *Schizochytrium* sp. as deposited, with mixotrophic character, and having a high yield of polyunsaturated fatty acids and carotenoids, such as DHA and astaxanthin, in the presence of an illumination that is variable and/or discontinuous over time.

It appeared that variable and/or discontinuous illumination of the cultures, in particular when used in a culture in mixotrophic mode, had a favourable impact on the development of the protists and made it possible to increase the productivity of the latter, notably as far as their lipid and carotenoid production is concerned. Without being bound to theory, the inventor believes that a discontinuous and/or variable light supply to the protists has the effect of causing a "stress" favourable to the growth and to the synthesis of lipids, as well as to the synthesis of carotenoids. This phenomenon may be partly explained by the fact that, in nature, protists tend to accumulate lipid and carotenoid reserves to withstand the constraints of their environment.

By "discontinuous illumination", it is meant an illumination punctuated by periods of darkness. The periods of darkness may be more than a quarter of the time, preferably, half of the time or more, during which the algae are cultured.

According to a preferred aspect of the invention, the illumination is discontinuous and, more preferentially in the form of flashes. A flash, within the meaning of the invention, is an illumination with light of short duration, i.e. of less than 30 minutes. The duration may be less than 15 minutes, preferably less than 5 minutes or even more preferentially less than 1 minute. According to certain embodiments of the invention, the duration of the flash may be less than a second. For example, the duration of the flash may be $1/10$ of a second, or $2/10$ of a second, or $3/10$ of a second, or $4/10$ of a second, or $5/10$ of a second, or $6/10$ of a second, or $7/10$ of a second, or $8/10$ of a second, or $9/10$ of a second. The illumination with light, or the flash, generally lasts longer than 15 seconds. It is generally comprised between 5 seconds and 10 minutes, preferably between 10 seconds and 2 minutes, more preferentially between 20 seconds and 1 minute.

In general, the number of flashes is comprised between about 2 and 3,600 per hour. It may be, for example, comprised between 100 and 3,600 flashes per hour. It may also be comprised between 120 and 3,000, or between 400 and 2,500, or between 600 and 2,000, or between 800 and 1,500 flashes per hour. It may also be comprised between 2 and 200, preferentially between 10 and 150, more preferentially between 15 and 100, and even more preferentially between 20 and 50 per hour. The flashes may be emitted at regular or irregular time intervals. In the case of emission at regular intervals, the number of flashes per hour then corresponds to a frequency (F) having a time period (T), it being considered that F=1/T. This time period may be comprised between 1 second and 30 minutes, or between 1 second and 36 seconds, or between 1.2 second and 30 seconds, or between 1.44 second and 9 seconds, or between 1.8 second and 6 seconds, or between 2.4 seconds and 4.5 seconds. This frequency may also be comprised between 18 seconds and 30 minutes, preferentially between 24 seconds and 6 minutes, more preferentially between 36 seconds and 4 minutes, and even more preferentially between 72 seconds and 3 minutes. The number of flashes per hour is selected as a function of the intensity and duration of the flashes (see below). In general, the intensity of the light supplied in the form of flashes is between 5 and 1,000 $\mu mol \cdot m^{-2} \cdot s^{-1}$, preferably between 5 and 500 $\mu mol \cdot m^{-2} \cdot s^{-1}$, or 50 and 400 $\mu mol \cdot m^{-2} \cdot s^{-1}$, and more preferentially between 150 and 300 $\mu mol \cdot m^{-2} \cdot s^{-1}$. 1 $\mu mol \cdot m^{-2} \cdot s^{-1}$ corresponds to 1 $\mu E\ m^{-2} \cdot s^{-1}$ (Einstein), a unit often used in the literature.

According to a particular embodiment of the invention, the intensity of the light is comprised between 50 and 200 $\mu mol \cdot m^{-2} \cdot s^{-1}$, the time period of the frequency of the flashes is comprised between 10 seconds and 60 minutes for a flash duration comprised between 1 second and 1 minute.

According to another embodiment of the invention, the illumination may be variable, which means that the illumination is not interrupted by phases of darkness, but instead the light intensity varies over time. This variation of the light intensity is regular and may be periodic or cyclic. According to the invention, light may also be supplied combining phases of continuous and discontinuous illumination.

According to the invention, regardless of the illumination conditions, the light intensity supplied to the algae in culture, expressed in micromoles of photons per second per square meter ($\mu mol \cdot m^{-2} \cdot s^{-1}$), varies at least once in any one hour. The amplitude of this variation of light intensity is generally comprised between 5 and 1,000, or between 50 and 800, or between 100 and 600 $\mu mol \cdot m^{-2} \cdot s^{-1}$. The intensity of the light may also vary between 5 and 400 $\mu mol \cdot m^{-2} \cdot s^{-1}$. Preferably, the amplitude of the variation of light intensity is between 70 and 300 $\mu mol \cdot m^{-2} \cdot s^{-1}$ and more preferentially between 100 and 200 $\mu mol \cdot m^{-2} \cdot s^{-1}$.

Said light intensity may attain successively, under conditions of variable illumination, for example, the values 50 $\mu mol \cdot m^{-2} \cdot s^{-1}$ and 100 $\mu mol \cdot m^{-2} \cdot s^{-1}$, or 5 and 400 $\mu mol \cdot m^{-2} \cdot s^{-1}$, or 50 and 800 $\mu mol \cdot m^{-2} \cdot s^{-1}$ several times every hour. Said light intensity may attain successively, preferably, the values 50 and 200 $\mu mol \cdot m^{-2} \cdot s^{-1}$. Alternatively, under conditions of discontinuous illumination, said light intensity may attain successively, several times per hour, for example, the values 0 and 50 $\mu mol \cdot m^{-2} \cdot s^{-1}$, the values 0 and 100 $\mu mol \cdot m^{-2} \cdot s^{-1}$ or more preferentially the values 0 and 200 $\mu mol \cdot m^{-2} \cdot s^{-1}$. It may also attain successively, several times per hour, for example, the values 0 and 300 $\mu mol \cdot m^{-2} \cdot s^{-1}$, the values 0 and 600 $\mu mol \cdot m^{-2} \cdot s^{-1}$, the values 0 and 800 $\mu mol \cdot m^{-2} \cdot s^{-1}$ or again the values 0 and 1,000 $\mu mol \cdot m^{-2} \cdot s^{-1}$.

According to an embodiment of the invention, regardless of the illumination conditions, the intensity of the light supplied to the culture varies as a function of the cell density. The denser the culture becomes, the more intense the light may be. The cell density is the number of cells per ml and it is measured by the techniques known to one skilled in the art.

At the initial stage of the culture, when the cell density is between about $10^5$ and $5 \times 10^5$ cells per ml, the light intensity may be between 5 and 15 $\mu mol \cdot m^{-2} \cdot s^{-1}$, preferably between 5 and 10 $\mu mol \cdot m^{-2} \cdot s^{-1}$. When the culture reaches a density between $10^6$ and $10^7$ cells per ml, the light intensity may be increased to between 15 and 200 $\mu mol \cdot m^{-2} \cdot s^{-1}$, for example, preferably between 20 and 50 $\mu mol \cdot m^{-2} \cdot s^{-1}$. When the culture, at the final stage, reaches a density between $10^7$ and $10^8$ cells per ml, the light intensity may be increased to between 50 and 700 $\mu mol \cdot m^{-2} \cdot s^{-1}$, for example, preferably between 50 and 150 $\mu mol \cdot m^{-2} \cdot s^{-1}$.

According to certain embodiments, for example, when the duration of the flashes is for example less than a minute, or less than a second, the intensity of the light may be higher than the values stated above. At the initial stage of the culture, when the cell density is between about $10^5$ and $5 \times 10^5$ cells per ml, the light intensity may be between 5 and 200 $\mu mol \cdot m^{-2} \cdot s^{-1}$, preferably between 5 and 100 $\mu mol \cdot m^{-2} \cdot s^{-1}$. When the culture reaches a density between $10^6$ and $10^7$ cells per ml, the light intensity may be increased to between 30 and 500 $\mu mol \cdot m^{-2} \cdot s^{-1}$, for example, preferably, between 50 and 400 $\mu mol \cdot m^{-2} \cdot s^{-1}$. When the culture, at the final stage, reaches a density between $10^7$ and $10^8$ cells per ml, the light intensity may be increased to between 100 and 1,000 $\mu mol \cdot m^{-2} \cdot s^{-1}$ for example, preferably, between 200 and 500 $\mu mol \cdot m^{-2} \cdot s^{-1}$.

According to an embodiment of the invention, the quantity of light supplied to the culture per hour remains between certain values. It is comprised between about 2,000 and 600,000, preferably between 2,000 and 300,000 $\mu mol \cdot m^{-2}$. It may be comprised between about 4,000 and 200,000 $\mu mol \cdot m^{-2}$, per hour.

According to an embodiment of the invention, the culture is illuminated with 30 flashes per hour, each flash having a duration of 30 seconds and an intensity of 10 $\mu mol \cdot m^{-2} \cdot s^{-1}$. The latter gives a total supply of light per hour of 9,000 $\mu mol \cdot m^{-2}$. According to another embodiment of the invention, the culture is illuminated with 20 flashes per hour, each flash having a duration of 30 seconds and an intensity of 20 $\mu mol \cdot m^{-2} \cdot s^{-1}$. The latter gives a total supply of light per hour of 12,000 $\mu mol \cdot m^{-2}$. According to another embodiment of the invention, the culture is illuminated with 45 flashes per hour, each flash having a duration of 15 seconds and an intensity of 5 $\mu mol \cdot m^{-2} \cdot s^{-1}$, which gives a total supply of light per hour of 3,375 $\mu mol \cdot m^{-2}$.

According to another embodiment of the invention, the culture is illuminated with 120 flashes per hour, each flash having a duration of 10 seconds and an intensity of 200 $\mu mol \cdot m^{-2} \cdot s^{-1}$, which gives a total supply of light per hour of 240,000 $\mu mol \cdot m^{-2}$.

As described for the light intensity above, and according to an embodiment of the invention, the quantity of light supplied to the culture per hour may vary as a function of the cell density. At the initial stage of the culture when the cell density is between $10^5$ and $5 \times 10^5$ cells per ml, the total supply of light per hour is generally comprised between about 1,500 and 8,000, preferably 1,500 and 6,000 $\mu mol \cdot m^{-2}$, more preferably between 2,000 and 5,000 $\mu mol \cdot m^{-2}$. When the culture reaches a density between $10^6$ and $10^7$ cells per ml, the total supply of light per hour may be increased to between 6,000 and 67,000 $\mu mol \cdot m^{-2}$, preferably between 6,000 and 50,000 and more preferably between 12,000 and 45,000 $\mu mol \cdot m^{-2}$, for example. At the final stage of the culture, at a cell density between $10^7$ and $10^8$ cells per ml, the total supply of light per hour may be increased to between 45,000 and 300,000, for example preferably between 45,000 and 200,000 $\mu mol \cdot m^{-2}$, and for example, yet more preferably, between 50,000 and 150,000 $\mu mol \cdot m^{-2}$.

According to an embodiment of the invention, in the initial stage of the culture (at a cell density between $10^5$ and $5 \times 10^5$ cells per ml), the culture is illuminated with 30 flashes per hour, each flash having a duration of 30 seconds and an intensity between 5 and 10 $\mu mol \cdot m^{-2} \cdot s^{-1}$, which gives a total supply of light per hour from 2,250 $\mu mol \cdot m^{-2}$ to 4,500 $\mu mol \cdot m^{-2}$. Then, at the intermediate stage (at a cell density between $10^6$ and $10^7$ cells per ml), the culture is illuminated with 30 flashes per hour, each flash having a duration of 30 seconds and an intensity between 15 and 50 $\mu mol \cdot m^{-2} \cdot s^{-1}$, which gives a total supply of light per hour of 13,500 to 45,000 $\mu mol \cdot m^{-2}$. Then, at the final stage of the culture (at a cell density between $10^7$ and $10^8$ cells per ml), the culture is illuminated with 30 flashes per hour, each flash having a duration of 30 seconds and an intensity between 50 and 150 $\mu mol \cdot m^{-2} \cdot s^{-1}$, which gives a total supply of light per hour of 45,000 to 135,000 $\mu mol \cdot m^{-2}$.

According to an embodiment of the invention, for example when the duration of the flashes is for example less than a minute, or less than a second, in the initial stage of culture (at a cell density between $10^5$ and $5 \times 10^5$ cells per ml), the culture is illuminated with 30 flashes per hour, each flash having a duration of 10 seconds and an intensity between 50 and 100 $\mu mol \cdot m^{-2} \cdot s^{-1}$, which gives a total supply of light per hour from 15,000 $\mu mol \cdot m^{-2}$ to 30,000 $\mu mol \cdot m^{-2}$. Then at the intermediate stage (at a cell density between $10^6$ and $10^7$ cells per ml), the culture is illuminated with 50 flashes per hour, each flash having a duration of 10 seconds and an intensity between 200 and 300 $\mu mol \cdot m^{-2} \cdot s^{-1}$, which gives a total supply of light per hour of 100,000 to 150,000 $\mu mol \cdot m^{-2}$. Then, at the final stage of the culture (at a cell density between $10^7$ and $10^8$ cells per ml), the culture is illuminated with 120 flashes per hour, each flash having a duration of 10 seconds and an intensity between 350 and 450 $\mu mol \cdot m^{-2} \cdot s^{-1}$, which gives a total supply of light per hour of 420,000 to 540,000 $\mu mol \cdot m^{-2}$.

The light supply to the cultures may be obtained by lamps distributed around the external wall of the fermenters. A clock triggers these lamps for defined illumination times. The fermenters are preferentially located in an enclosure, shielded from daylight, whose ambient temperature may be controlled.

As the applicant could ascertain, the fact that the thus selected strains have good growth capabilities in mixotrophic mode, in the presence of discontinuous and/or variable light, predisposes said strains to a higher production of polyunsaturated fatty acids and carotenoids, notably DHA and astaxanthin.

The method of culture according to the invention thus allows selection of strains of the Labyrinthulomycetes class, notably of the Thraustochytrid families, in particular of the genus *Schizochytrium*, with mixotrophic character, similar to that isolated by the applicant and deposited at the CCAP under the accession number CCAP 4087/1, and having a high yield of polyunsaturated fatty acids and carotenoids. This method of culture is characterized in that it comprises the following steps:

a) culture, in mixotrophic mode, of one or more strains of the Labyrinthulomycetes class, in particular, of the genus *Schizochytrium* under conditions of illumination that is discontinuous and/or variable over time, the illumination having variations in intensity, the amplitude of which is comprised between 5 $\mu mol \cdot m^{-2} \cdot s^{-1}$ and 1,000, preferably between 5 and 400 $\mu mol \cdot m^{-2} \cdot s^{-1}$, these variations taking place between 2 and 3,600, preferably 5-400 times per hour, b) a step of maintaining said culture over several generations, in the presence of an organic carbon-containing substrate in the culture medium, and optionally c) a step of recovery of the thus cultured protists.

By "step of recovery", it is meant more particularly the isolation of the strain or strains for which the number of cells increased the most during said generations.

For carrying out selection of the strains, different strains of the Labyrinthulomycetes class, notably the Thraustochytrid family, in particular of the genus *Schizochytrium*, may be cultured, in parallel, on microplates in one and the same enclosure, with precise monitoring of the conditions and evolution of the different cultures. It is, thus, easy to determine the response of the different strains to discontinuous and/or variable illumination and, if applicable, to the addition of one or more organic carbon-containing substrates to the culture medium. The strains that respond favourably to the discontinuous and/or variable illumination and to the organic carbon-containing substrates, generally provide a better yield for the production of carotenoids and lipids in terms of quality (polyunsaturated fatty acids more abundant in the lipid profile and astaxanthin more abundant among the carotenoids) and in terms of quantity (the lipids contain a higher proportion of DHA and the dry matter comprises a higher proportion of astaxanthin).

The protists may be selected in a fermenter from a heterogeneous population, and from which one aims to select the variants favoured by the manner of selection according to the invention, combining discontinuous and/or variable light, having a specific range of light intensity and a specific frequency, with mixotrophic culture conditions. In this case, culture is carried out by maintaining the protists in culture over many generations, and then an isolation of the components that have become predominant in the culture medium, is performed at the end of culture.

The method of culture according to the invention also makes it possible to produce lipids and carotenoids.

In this case, the method according to the invention further comprises the following steps:

d) a step of recovery of the hydrophobic matter of the protists, and optionally e) the extraction of DHA (docosahexaenoic acid) and astaxanthin from the recovered hydrophobic matter.

The hydrophobic matter in fact comprises the lipids and the carotenoids.

The method of culture according to the invention may also be applied to any species of the genus *Schizochytrium*, capable of growing under the mixotrophic conditions according to the invention, and capable of producing DHA and astaxanthin.

The method of culture according to the invention makes it possible to optimize the production of the biomass obtained from the culture. It also makes it possible to enrich the thus cultured protists in polyunsaturated fatty acids and carotenoids, more particularly in docosahexaenoic acid (DHA) and astaxanthin.

Therefore, the invention is also directed to optimizing the production of biomass, as well as the production of lipids and carotenoids, notably of fatty acids, through the culture of protists of the genus *Schizochytrium* with mixotrophic character, preferably cultured or selected according to the methods mentioned above, then the recovery of the thus cultured protists in order to extract the hydrophobic content therefrom, in particular the lipids including DHA, and the carotenoids, including astaxanthin.

The methods for selectively extracting the lipids, including DHA, are known to one skilled in the art and are, for example, described by [Bligh, E. G. and Dyer, W. J. (1959); A rapid method of total lipid extraction and purification, Can. J. Biochem. Physiol., 37: 911-917].

The methods of extraction and analysis of the carotenoids, including lutein, are known to one skilled in the art and are, for example, described by Wright et al. (1991) (S. W. Wright, S. W. Jeffrey, R. F. C. Mantoura, C. A. Llewellyn, T. Bjornland, D. Repeta, N. Welschmeyer: Improved HPLC method for the analysis of chlorophylls and carotenoids from marine phytoplankton. Marine Ecology Progress Series: Vol. 77: 183-196, 1991).

The invention also relates to the protist strains of the Labyrinthulomycetes class, notably of the Labyrinthulid and Thraustochytrid families, in particular of the genus *Schizochytrium*, which can be obtained according to the method of the invention as described above. These protists are enriched in polyunsaturated fatty acids and carotenoids. The total lipids of such protists generally comprise more than 40%, or more than 50%, or more than 60% of DHA relative to the total percentage of lipids. The astaxanthin contained in such protists, according to an embodiment of the invention, may represent more than 0.1%, or more than 0.15%, or more than 0.2% by weight of the total weight of dry matter. The protists according to an embodiment of the invention may thus have a productivity (quantity of product of interest produced, per liter of culture, per hour) of astaxanthin of 0.015 mg/L/h, or more than 0.020 mg/L/h, or more than 0.025 mg/L/h.

Example 1

The cultures of *Schizochytrium* are carried out in 1 to 2 L usable capacity fermenters (bioreactors) with dedicated automatic controllers and computerized supervision. The pH of the system is adjusted by adding base (a 2N sodium hydroxide solution) and/or acid (a 1N sulphuric acid solution). The culture temperature is set to 26° C. Stirring is achieved using 3 stirring rotors mounted on the shaft according to the Rushton configuration (three-blade impellers with downward pumping). The dissolved oxygen pressure is regulated in the medium throughout culture, by the stirring speed (250-600 rpm), the air flow rate (0.25-1 vvm), or the oxygen flow rate (0.1-0.5 vvm). The control parameters, integrated into the automatic system for supervision, make it possible to maintain a constant $pO_2$ at 15%. The bioreactor is equipped with an external lighting system surrounding the transparent tank. The intensity as well as the light cycles is controlled by a dedicated automatic device, under computerized supervision.

The reactors are inoculated with a preculture prepared on a stirring table (140 rpm) in a controlled-temperature enclosure (26° C.) and illuminated between 100 and 200 µE. Pre-cultures and cultures in the bioreactors are carried out in the modified Verduyn medium (sea salts 15 g/L, $(NH_4)_2SO_4$ 3 g/L, $KH_2PO_4$ 1 g/L, $MgSO_4.7H_2O$ 0.5 g/L, $Na_2EDTA$ 24 mg/L, $ZnSO_4.7H_2O$ 3 mg/L, $MnCl_2.2H_2O$ 3 mg/L, $Na_2MoO_4.2H_2O$ 0.04 mg/L, $FeSO_4.7H_2O$ 10 mg/L, pantothenate 3.2 mg/L, thiamine hydrochloride 9.5 mg/L, vitamin B12 0.15 mg/L). The carbon-containing substrate used for the culture under conventional mixotrophic conditions, under heterotrophic conditions and under mixotrophic conditions with flash (variable/discontinuous light) in the bioreactor is glucose at concentrations between 300 mM and 1 M.

Monitoring of the Cultures:

The total biomass concentration is monitored by measuring the dry mass (filtration on a Whatman GF/F filter, then oven drying, at 105° C., for min. 24 h before weighing).

Regarding the quantification of the total lipids, $10^8$ cells/mL were extracted. Methods for extracting lipids are known to one skilled in the art.

For the quantification of the carotenoids and notably astaxanthin, $10^8$ cells/mL were extracted. Methods for extraction and analysis of the carotenoids, including astaxanthin, are known to one skilled in the art.

Illumination (for Culture Under Mixotrophic Conditions):

The culture is illuminated with 30 flashes per hour, each flash having a duration of 30 seconds and an intensity of 80 $\mu mol \cdot m^{-2} \cdot s^{-1}$.

The light supply to the cultures in the bioreactor was obtained by LED (light-emitting diode) lamps distributed around the external wall of the fermenter. A clock triggers these LED lamps for illumination times or pulses (for culture under flash mixotrophic conditions with discontinuous light).

Results (n=3):

|  | Dry mass (g/L) | Total lipids (% of dry mass) | % DHA | Astaxanthin (mg/g of dry mass) |
| --- | --- | --- | --- | --- |
| Mixotrophy with flashes | 140 ± 2.1 | 28 ± 0.6 | 43 ± 1.8 | 2 ± 0.1 |
| Heterotrophy | 118.1 ± 2.5 | 28.8 ± 0.6 | 45.2 ± 2 | 0 |

The invention claimed is:

1. A method of producing docosahexanoic acid (DHA) and astaxanthin in a culture of protists lacking chloroplasts of the genus *Schizochytrium*, comprising the following step:
   a) culturing of one or more strains of *Schizochytrium* over several generations in a culture medium containing an organic carbon-containing substrate, under conditions of alternation of illuminated phases and phases of darkness,
   wherein the illumination is provided in the form of flashes of light,
   each flash having an intensity between 5 $\mu mol \cdot m^{-2} \cdot s^{-1}$ and 1,000 $\mu mol \cdot m^{-2} \cdot s^{-1}$, said flashes of light occurring between 2 and 3,600 times per hour, and
   wherein said phases of darkness occupy more than half of the time during which said strains of *Schizochytrium* are cultured.

2. The method according to claim 1, wherein the culture is carried out in the presence of an organic carbon-containing substrate at a concentration 300 mM to 1.2 M, the organic carbon-containing substrate being at least one selected from the group consisting of saccharose, glycerol, glucose, cellulose derivatives, and a mixture thereof.

3. The method according to claim 2, wherein the concentration of the at least one organic carbon-containing substrate is from 600 mM to 900 mM.

4. The method according to claim 1, wherein the total light supply per hour in micromoles of photons is between 2,000 to 600,000.

5. The method according to claim 1, further comprising the following steps:
   b) recovering the thus cultured protists, and optionally
   c) recovering the DHA and astaxanthin from the recovered protists.

6. The method according to claim 1, wherein said protists of the genus *Schizochytrium* corresponds to the strain FCC 1104, deposited at the CCAP (Culture Collection of Algae and Protozoa), under number CCAP 4087/1.

7. The method according to claim 1, wherein said flashes of light have an intensity between 50 and 400 $\mu mol \cdot m^{-2} \cdot s^{-1}$.

8. The method according to claim 1, wherein said flashes of light have a duration of between 5 seconds and 10 minutes.

9. The method according to claim 1, wherein said flashes of light have a duration of between 20 seconds and 1 minute.

10. The method according to claim 1, wherein the number of flashes is between 10 and 150 times per hour.

11. The method according to claim 1, wherein the number of flashes is between 20 and 50 times per hour.

12. The method according to claim 1, wherein said at least one organic carbon-containing substrate is at least 300 mM of glucose and/or glycerol.

13. The method according to claim 1, wherein the cultured protists have a productivity (quantity of DHA and astaxanthin produced, per liter of culture, per hour) of at least 0.015 mg/L/h.

14. The method according to claim 1, wherein the cultured protists have a productivity (quantity of DHA and astaxanthin produced, per liter of culture, per hour) of more than 0.025 mg/L/h.

15. The method according to claim 1, wherein the cultured *Schizochytrium* produces DHA in an amount representing more than 40% of the total lipids contained in the *Schizochytrium*.

16. The method according to claim 1, wherein the cultured *Schizochytrium* produces DHA in an amount that represents more than 60% of the total lipids contained in the *Schizochytrium*.

17. The method according to claim 1, wherein the cultured *Schizochytrium* produces astaxanthin in an amount that represents more than 0.1% of the total weight of dry matter.

18. The method according to claim 1, wherein the cultured *Schizochytrium* produces astaxanthin in an amount that represents more than 0.2% of the total weight of dry matter.

* * * * *